United States Patent [19]
Waters

[11] Patent Number: 5,254,750
[45] Date of Patent: Oct. 19, 1993

[54] REMOVAL OF GUAIACOL FROM CRESYLIC ACID BY HEATING WITH A STRONG BASE

[75] Inventor: John A. Waters, Houston, Tex.

[73] Assignee: Merichem Company, Houston, Tex.

[21] Appl. No.: 42,550

[22] Filed: Apr. 5, 1993

[51] Int. Cl.$^5$ .................. C07C 37/68; C07C 37/70
[52] U.S. Cl. .................. 568/749; 568/748; 568/750
[58] Field of Search .................. 568/749, 750, 748

[56] References Cited

U.S. PATENT DOCUMENTS

| | | |
|---|---|---|
| 4,381,413 | 4/1983 | Dodd . |
| 4,473,713 | 9/1984 | Ratton . |
| 5,146,010 | 9/1992 | Brient et al. . |
| 5,171,895 | 12/1992 | Brient . |
| 5,177,269 | 1/1993 | Waters et al. .................. 568/749 |

FOREIGN PATENT DOCUMENTS 2012730 1/1987 Japan .

OTHER PUBLICATIONS

Lawson et al "Influence of Water on Guaiacol Pyrolysis", Ind. Eng. Chem Fundam. vol. 24: pp. 203-208 1985.

*Primary Examiner*—Werren B. Lone
*Attorney, Agent, or Firm*—John R. Kirk, Jr.

[57] ABSTRACT

A process is described for the removal of guaiacol and substituted guaiacols from naturally occurring cresylic acid feed by heating the feed with a strong base, particularly sodium hydroxide, to produce a purified cresylic acid product essentially free of guaiacol and other methoxy aromatic compounds without significant loss of cresylic acid product.

14 Claims, No Drawings

REMOVAL OF GUAIACOL FROM CRESYLIC ACID BY HEATING WITH A STRONG BASE

FIELD OF THE INVENTION

This invention relates to a process for removing alkoxyaromatic impurities, particularly guaiacol and substituted guaiacols, from naturally occurring cresylic acid feeds by heating with a strong base, particularly sodium hydroxide.

BACKGROUND OF THE INVENTION

Cresylic acid is an important commercial product widely used in the manufacture of chemical, agrichemical, pharmaceutical, and industrial intermediate products. Unfortunately, very few cresylic acid members are commercially synthesized. For example, the lowest molecular weight member of the cresylic acid family, phenol, is produced synthetically in very large quantities. Similarly, the methylphenols (known as cresols) are also produced synthetically, but in much smaller quantities. On the other hand, the dimethylphenols (known as xylenols) and other alkylated phenols are not commercially synthesized to any appreciable extent with the exception of 2,6-xylenol. As such, the majority of cresylic acid isomers used in industry today are recovered from natural sources, such as partially refined petroleum and coal via coking, gasification, and liquefaction The cresylic acid recovered from these sources, however, is heavily contaminated with aromatic organic compounds including hydrocarbons containing heteroatoms such as nitrogen, sulfur, and oxygen. These impurities must be removed in order to make marketable products. Methoxy-substituted phenols, such as guaiacol and methyl guaiacol, comprise a particularly troublesome group of contaminants Since guaiacol, an ortho-methoxy phenol, boils near the boiling points of meta-cresol and para-cresol, and methyl guaiacol, a methoxy cresol, boils in the range of xylenols, they cannot be separated from the cresylic acid fractions by conventional distillation. The presence of such methoxyaromatic impurities significantly reduces the commercial value of cresylic acid as a raw material for high quality plastics and resins. To be useful, the various isomers of cresylic acid must be separated from these impurities and often from each other, and therein lies the problem because, heretofore, there has been no simple process for physically or chemically separating guaiacols from cresylic acid. In the past, the guaiacol was destroyed in the presence of the cresylic acid but with a considerable decrease in cresylic acid yield. Moreover, such destruction had been accomplished only with much difficulty and with the resultant loss of cresylic acid yield to byproducts, most of them unwanted heavies and coke.

Considerable academic research has been reported relating to the removal of methoxy compounds and to the demethylation of phenols. This work is reported in articles, such as J. Lawson and M. Klein, "Influence of Water on Guaiacol Pyrolysis," *Ind. Eng. Chem. Fundam.*, 24:203, 1985; R. Ceylan and J. Bredenberg, "Hydrogenolysis and Hydrocracking of the Carbon-Oxygen Bond. 2. Thermal Cleavage of the Carbon-Oxygen Bond in Guaiacol," *Fuel*, 61:377, 1982; and A. Vuori and J. Bredenberg, "Hydrogenolysis and Hydrocracking of the Carbon-Oxygen Bond. 4. Thermal and Catalytic Hydrogenolysis of 4-Propylguaiacol," *Holzforschung*, 38:133, 1984.

Likewise, a dealkylation process involving the reaction of acetic acid in the presence of an alumina-silica catalyst in the liquid phase is described in U.S. Pat. No. 2,697,732. The rearrangement of alkyl phenyl ethers to ortho-alkyl phenols by heating at temperatures from 75° C. to 200° C. in the presence of alumina is described in U.S. Pat. Nos. 4,447,657 and 4,381,413. A process for the hydrolysis of alkyl-aryl ethers in the presence of a carboxylate, preferably an alkali metal carboxylate, catalyst is described in U.S. Pat. No. 4,473,713. Recent processes have described the removal of guaiacols by pyrolysis (U.S. Pat. No. 5,146,010) and U.S. Pat. No. 5,177,269 describes a process for the removal of guaiacol from naturally occurring cresylic acid feed by heating the feed with a strong acid, particularly hydrochloric acid or sulfuric acid, to produce a guaiacol free product.

Notwithstanding the considerable amount of investigation of this problem of guaiacol removal, the search for totally satisfactory results continues. It is an object of this invention to provide a process for the destruction of guaiacols in the presence of cresylic acids so they may be used for other purposes.

SUMMARY OF THE INVENTION

This invention is a process for the removal of guaiacol impurities from a naturally occurring cresylic acid feedstream, especially for a feedstream derived from lignite sources, by heating the feed in the presence of a strong base, to produce a purified cresylic acid product essentially free of guaiacol and other methoxy aromatic compounds without significant loss of cresylic acid product or coke formation. Strong bases useful in the practice of this invention include those having a dissociation constant, K, less than about $10^{-12}$ or, said another way, a pH of greater than about 12. Classes of bases such as the alkali metal hydroxides, for example, lithium hydroxide, sodium hydroxide, and potassium hydroxide, and other hydroxide bases, for example, magnesium hydroxide, aluminum hydroxide, and ammonium hydroxide are preferred.

The process is normally practiced at a temperature range of from about 50° C. to about 350° C. for a sufficient time period normally from about 1 hour to about 8 hours, depending upon base strength, ratio of base to feed, and temperature. Pressure is normally a function of the temperature of the contents of the closed reactor. Base strength ranges from about 15% to about 60% by weight and with a molar excess of the base (100% basis) being present than that required to neutralize the cresylic acid present in the reaction mixture to improve guaiacol reduction, while preventing unwanted byproduct formation, and coke and gas formation. Variations in the cresylic acid feed matrix, depending upon the source and guaiacol levels in the feed, are also considered in determining the reaction conditions and may require a greater or lesser molar excess of base being present.

DETAILED DESCRIPTION OF THE INVENTION

This invention is a process for the purification of naturally occurring cresylic acid mixtures recovered from the pitch residue in the removal of liquids from coal, coal tars, lignite, or natural gas condensates. These naturally occurring cresylic acid-containing mixtures include several species of methoxyaromatic impurities, particularly guaiacol, which is often present in amounts up to about 4% and sometimes about 6% by weight in feed material which comes from a lignite source and about 2% where the feed material for the practice of this invention is recovered from coal or coal tar. The process of this invention would successfully operate to eliminate even greater amounts of guaiacol in naturally occurring feeds and should not be considered limited to one containing 4% by weight. To treat a feed containing higher guaiacol levels, a higher base/cresol molar ratio is used.

To begin, the crude feed is usually treated to remove residual pitch and distilled to remove phenols and low-boiling hydrocarbons, i.e., those materials which have boiling points below or near that of the phenol being removed. The feed is then heated in a closed vessel in the presence of a strong base, preferably sodium hydroxide (either fed to the system in aqueous form or as pellets), usually with agitation, as more particularly described below.

While sodium hydroxide is especially preferred in the practice of this invention, it should be understood that strong bases useful in the practice of this invention includes those having a dissociation constant, K, less than about $10^{-12}$. Classes of such bases include the alkali metal hydroxides, for example, lithium hydroxide, sodium hydroxide, and potassium hydroxide, calcium hydroxide, and other metal hydroxide bases, for example, magnesium hydroxide, aluminum hydroxide, and ammonium hydroxide. Those skilled in the art desiring to produce cresylic acid mixtures readily useful in other processes would, of course, know to avoid certain strong bases even though they fit within the criteria set forth above if side reactions or byproduct creation results in a product which is not satisfactory. As will be seen hereafter, it is the degree of dissociation of the base and not the concentration of the base which is important in connection with the practice of this invention. However, using the disclosure which follows and the specific examples in connection with the degree of dilution of sodium hydroxide, knowing the strengths of such bases which are commercially available, one of ordinary skill in the art can readily determine the concentrations of the above-identified strong bases useful in the practice of this invention.

In its broad context, the practice of this invention would occur in a batch reactor, preferably one impervious to attack by dilute aqueous solutions of strong bases. A stainless steel reactor has been used in the practice of this invention, but may eventually be subject to embrittlement at high temperatures. A more tolerant metal is a nickel alloy such as, for example, monel. The strong base should preferably be used in an aqueous form, normally from about 15% to about 60% by weight, preferably from about 25% to about 55% by weight, particularly when the strong base is sodium hydroxide or, alternatively, the base may be in pellet form without being dissolved in water. The preferred strength of the aqueous sodium hydroxide would preferably range from about 45% to about 50% by weight. The aqueous base, in the strength as described above, is added to the reactor containing the feed stream in an amount such that the aqueous base is present in the mixture in a molar excess of the amount necessary to neutralize the cresylic acid present, preferably from about 10% to about 50% molar excess. The selection of the amount of excess depends upon the economics involved and the degree to which unwanted side reactions may result. Preferably, the molar ratio of base to cresylic acid is from about 1.1:1 to about 1.5:1 (100% basis). Of course, the more base with respect to the feed present, on a molar basis, the faster the reaction would occur, and therefore the lower the temperature required.

Once the reactants are present together, the reaction vessel would be closed and rendered pressure-tight and brought to a temperature of from about 50° C. to about 350° C., preferably from about 200° C. to about 300° C. and, preferably with stirring, allowed to react for an effective period of time, preferably from about 1 to about 8 hours, more preferably from about 4 to about 6 hours. Of course, the time and temperature, as well as the strength of the aqueous solution of the strong base used, determine the results of the guaiacol removal and the amount of byproducts or tars formed. The pressure in the reaction vessel would normally be autogenous pressure for the temperature and reaction condiions run but would be found to vary from about 100 psig to about 400 psig. The cresylic acid feeds will react differently under the process of this invention. The optimum conditions for the elimination of guaiacol within the foregoing parameters can readily be determined by routine experimentation, given the description of this invention.

Once the reaction is complete or the selected amount of time has passed, the reactor and its content are cooled. This cooling could be accomplished in any number of ways well known to those of ordinary skill in the art either by internal cooling coils or by flashing the reaction mixture into another vessel, or the like. Should the temperature not be reduced fairly rapidly, the presence of the strong base, particularly sodium hydroxide, results in further reaction to form unwanted byproducts and loss in yield of the cresylic acid product. Here again, the amount of excess based used is a consideration. After cooling, the reactants are neutralized with an acid such as, for example, hydrochloric acid, sulfuric acid, or phosphoric acid.

It is preferred that the cresylic acid, now substantially free of guaiacol, be separated from the aqueous base by solvent extraction of the organic product from the aqueous phase containing the base. Virtually an of the well known water-immiscible solvents for such cresylic acid-containing materials could be used but it is preferred that toluene be used to separate the organic layer from the aqueous layer present in the reaction mixture. The toluene, or organic, phase is separated from the aqueous phase and flashed or distilled in another appropriate manner to remove the solvent toluene from the cresylic acid product now substantially free of not only guaiacol but of nitrogen-containing aromatic compounds previously present in the reaction mixture. Alternatively, the anisoles that are formed may be distilled from the cresols. The guaiacol was shown to be hydrolyzed to phenol and catechol and byproducts included xylenols and methylanisoles, as well as high molecular weight coupled cresols. Impurity formation appeared to be a function of guaiacol conversion, both in amount and type of impurity produced.

Alternatively, the invention could be practiced as a continuous process. The cresylic acid feed could be presented at a flow rate, depending upon the size of the reaction equipment, to achieve a residence time of from about 3 hours to about 8 hours, preferably about 4 to 5 hours, at temperatures of from about 200° C. to about 500° C., preferably about 250° C. The pressure conditions for a continuous process would be of from about 250 psig to about 500 psig. The concentrations of the strong base normally would be of from about 15% to about 60% by weight.

The following examples are introduced to illustrate further the novelty and utility of the present invention but not with the intention of unduly limiting the same. The reactions were run in a closed, stainless steel autoclave (unless otherwise indicated) to minimize corrosion problems.

EXAMPLES

Example No. 1

In a teflon-coated, stirred autoclave, a 53 g synthetic mixture of meta-cresol/para-cresol containing 1.2% guaiacol was heated with 26 g of NaOH pellets dissolved in 30 g of water for 3 hours at 175° C. The pressure was estimated to be 50 psig. The next day, 200 ml of $H_2O$ were added at 70° C. The mixture was extracted with alcohol, neutralized with 55g of $H_2SO_4$, and extracted with alcohol again. When the cresylic mixture was flash distilled at 50° C. and 10 mm Hg, the distillate weighed 50.2 g and contained 0.069% guaiacol. Little or no byproducts were formed.

Example No. 2

A 20% solution of sodium hydroxide was prepared by dissolving 44.6 g (1.1 moles) of NaOH pellets in 178.5 g of water. From this solution was taken a sample weighing 111.6 g which was heated with a 56 g sample of meta-cresol/para-cresol (containing 2.8% guaiacol) for 6 hours at 250° C. in a 500 ml stainless steel autoclave. A sampling tube was piped into the reactor and 10 g samples were removed every hour. To each sample was added 10 ml of concentrated HCl and 10 ml of toluene. The bottles were shaken and the organic layer filtered. The organic layer was then neutralized with sodium carbonate ($Na_2CO_3$) and again filtered. It was then submitted for gas chromatographic analysis. The resulting cresylic acid mixture at the end of the sixth hour contained only 0.02% guaiacol and very little (0.05%) "heavies." The results are shown in Tables IA and IB. Table IA also shows the results of two other runs made as set forth above at different temperatures and for different times.

Example No. 3

A 50% solution of sodium hydroxide was prepared by dissolving 44.4 g of NaOH pellets in an equal amount of de-ionized water. The resulting solution was heated with 111.5 g of cresols (containing 2.8% guaiacol) for 5 hours at 250° C. in a stainless steel autoclave. Samples were taken every hour as before. At the end of the fourth hour, there was no detectible guaiacol in the cresol mixture. The concentration of heavy material was only 0.11%. The results are shown in Tables IIA and IIB. Following the procedure described, other runs were made, reported on Table IIA, at differing temperatures.

Example No. 4

A similar mixture of m/p cresols containing 2.8% guaiacol was heated for 5 hours with 44 g of sodium hydroxide pellets at 250° C. Hourly samples were analyzed as before. At the end of the second hour, the guaiacol content was too low to be detected. The concentration of heavy material was 0.37%. The results are shown in Tables IIIA and IIIB.

TABLE IA

DATA FROM RUNS USING 20% NaOH

| Moles of m/p-Cresol | Strength of Caustic (Wt %) in $H_2O$ | Molar Ratio NaOH/Cresol | Temp. °C. | Pressure (psig) | Time (hrs) | Starting Guaiacol Content (%) | Final Guaiacol Content (%) |
|---|---|---|---|---|---|---|---|
| 0.5 | 20 | 1.1/1 | 210 | 280 | 6 | 2.36 | 1.43 |
| 0.5 | 20 | 1.1/1 | 225 | 325 | 3 | 2.36 | 1.42 |
| 0.5 | 20 | 1.1/1 | 250 | 450 | 2.5 | 2.40 | 0.37 |

TABLE IB

DECREASE OF GUAIACOL WITH TIME USING 20% NaOH AT 250° C.
(Given in Units of Area % of Chromatograph Scan of Filtered Cresylics)

| Component | 1st Hour | 2nd Hour | 3rd Hour | 4th Hour | 5th Hour | 6th Hour |
|---|---|---|---|---|---|---|
| Methylanisoles | 0.31 | 0.38 | 0.22 | 0.70 | 0.85 | 0.85 |
| Guaiacol | 0.83 | 0.42 | 0.19 | 0.11 | 0.04 | 0.02 |
| Phenol + o-Cresol | 0.12 | 0.17 | — | 0.27 | 0.30 | 0.30 |
| OEP | 0.03 | 0.03 | — | 0.05 | 0.04 | 0.03 |
| 2,4/2,5 + p-Cresol | 31.93 | 32.01 | 32.14 | 31.85 | 32.20 | 31.38 |
| m-Cresol | 66.86 | 67.07 | 67.50 | 67.22 | 67.14 | 67.14 |
| Heavies | 0 | 0.03 | — | — | — | 0.05 |

TABLE IIA

DATA FROM RUNS USING 50% NaOH

| Moles of m/p-Cresol | NaOH Strength (Wt %) in $H_2O$ | Molar NaOH Cresol Ratio | Temperature °C. | Pressure (psig) | Time (hrs) | Final Guaiacol Content (wt %) |
|---|---|---|---|---|---|---|
| 0.5 | 30.25 | 1.3/1 | 165 | 130 | 3 | 2.13 |
| 0.5 | 31.00 | 0.25/1 | 170 | 90 | 1 | 2.08 |
| 0.5 | 46.00 | 1.3/1 | 188 | 130 | 3 | 2.00 |
| 0.5 | 46.00 | 1.3/1 | 200 | 150 | 3 | 0.75 |
| 0.5 | 46.00 | 1.3/1 | 225 | 200 | 3 | 0.91 |

TABLE IIB

DECREASE OF GUAIACOL CONTENT WITH TIME USING 50% NaOH AT 250° C.
(Area % of GLC for Filtered Undistilled Cresylic)*

| Component | 1st Hour | 2nd Hour | 3rd Hour | 4th Hour | 5th Hour |
|---|---|---|---|---|---|
| Methylanisoles | 0.67 | — | — | — | — |
| Guaiacol | 0.69 | 0.20 | — | — | — |
| Phenol + o-Cresol | 0.17 | 0.28 | 0.555 | 0.72 | 0.92 |
| OEP | 0.02 | 0.03 | 0.47 | 0.02 | 0.03 |
| 2,4, 2,5-Xyl, + p-Cresol | 31.91 | 31.90 | 0.03 | 31.71 | 31.13 |
| m-Cresol | 66.47 | 67.61 | 31.54 | 67.44 | 67.80 |
| Heavies | — | — | 67.88 | 0.11 | 0.23 |
|  |  |  | 0.08 |  |  |

NaOH/Cresol = 1.1 molar ratio.

TABLE IIIA

DATA FROM RUNS USING 100% NaOH

| Moles m/p Cresol | NaOH/Cresol Mole Ration | Temperature (°C.) | Pressure (psig) | Time (Hours) | Final Guaiacol Content (Wt %) |
|---|---|---|---|---|---|
| 0.74 | 1.31/1 | 225 | 80 | 3 | 0.371 |
| 0.74 | 1.31/1 | 270 | 150 | 4 | — |

TABLE IIIB

DECREASE OF GUAIACOL CONTENT WITH TIME USING 100% NaOH AT 250° C.
(Guaiacol Content Given As Area % For Filtered Undistilled Cresylic)

| Component | 1st Hour | 2nd Hour | 3rd Hour | 4th Hour | 5th Hour |
|---|---|---|---|---|---|
| Methylanisoles | 0.77 | 0.39 | 0.28 | 0.13 | 0.02 |
| Guaiacol | 1.27 | — | — | — | — |
| Phenol + o-Cresol | 0.12 | 1.24 | 1.78 | 2.44 | 3.06 |
| OEP | 0.03 | 0.03 | 0.17 | 0.29 | 0.38 |
| 2,4,2,5-Xyl. + p-Cresol | 29.01 | 31.07 | 30.08 | 29.76 | 29.24 |
| m-Cresol | 59.83 | 67.04 | 66.97 | 66.66 | 66.17 |
| Heavies | 0.03 | 0.37 | 0.57 | 0.81 | 1.11 |

Tables IB, IIB, IIIB show the decrease in guaiacol content with time using NaOH treatments at concentrations of 20%, 50%, and 100%, respectively, at 250° C. The dilute caustic soda at 20% in Table IB reveals that the guaiacol was still detectable after 6 hours with a small buildup of phenol and heavies. The 20% NaOH also required long reaction times and higher pressures. In contrast, Table IIB shows that the 50% caustic soda resulted in complete guaiacol removed in about 4 hours. An even faster reaction occurred in Table IIIB using the NaOH pellets without water. The guaiacol was removed in 2 hours; however, the rates of formation of phenol and higher boiling material were greater than with aqueous NaOH. From these experiments, the preferred conditions for complete guaiacol conversion appear to be about 50% aqueous NaOH at 250° C. for 4 hours with a stoichiometric (molar) ratio of 1.1 mols NaOH per mol cresol (10% excess).

The above description of embodiments and examples of this invention are given by way of example and instruction and are not intended as limitations to the claims which follow since further embodiments and changes will occur to those of skill in the art after reading the above description of the present invention.

What is claimed is:

1. A process for removing guaiacol impurities from a naturally occurring cresylic acid mixture which comprises the steps of:
   heating the cresylic acid mixture for a sufficient period of time in the presence of an aqueous solution of a strong base at a temperature of from about 50° C. to about 350° C. at autogenous pressure;
   cooling the mixture; and
   recovering the cresylic acid product from the mixture.

2. The process of claim 1 wherein the strong base is present in a molar excess.

3. The process of claim 2 wherein the strong base is an alkali metal hydroxide.

4. The process of claim 3 wherein the alkali metal hydroxide is sodium hydroxide.

5. The process of claim 2 wherein the molar excess of the strong base is from about 10% to about 50%.

6. The process of claim 1 wherein the cresylic acid product is recovered from the reaction mixture by solvent extraction.

7. The process of claim 6 wherein the solvent is toluene.

8. A process for removing guaiacol impurities from a naturally occurring cresylic acid mixture which comprises the steps of:
   heating the cresylic acid mixture in the presence of an aqueous solution of an alkali metal hydroxide, at a temperature of from about 50° C. to about 350° C. at autogenous pressure;
   cooling the mixture; and
   recovering the cresylic acid product from the mixture by solvent extraction wherein the solvent is toluene.

9. The process of claim 8 wherein the strong base is from about 15% to about 60% by weight sodium hydroxide at a temperature of from about 200° C. to about 300° C. at autogenous pressure for a time of from about 1 hours to about 8 hours.

10. A process for removing guaiacol impurities from a cresylic acid feed obtained from a lignite source which comprises the steps of:
heating the feed in the presence of from about 25% to about 55% concentration by weight of a strong base, present in a molar excess of base sufficient to neutralize the cresylic acid feed for a period of from 4 hours to about 6 hours at a temperature of from about 200° C. to about 300° C. at autogenous pressure to form a reaction mixture;
cooling the reaction mixture;
adding to the cooled reaction mixture a sufficient quantity of a water immiscible solvent selective for the feed in the reaction mixture allowing a phase separation to occur between the solvent containing the cresylic acid and the aqueous components;
separating the aqueous phase from the solvent phase; and
distilling the solvent from the cresylic acid product being substantially free of guaiacol.

11. The process of claim 10 wherein the solvent is toluene.

12. The process of claim 11 wherein the base is present in a molar excess of from about 10% to about 50%.

13. The process of claim 12 wherein the base is sodium hydroxide.

14. A continuous process for removing guaiacol impurities from a cresylic acid mixture which comprises the steps of:
heating the cresylic acid mixture at a temperature of from about 200° C. to about 500° C. at a pressure of from about 250 psig to about 500 psig in a reactor for a residence time of from about 3 hours to about 8 hours;
cooling the mixture; and
recovering the cresylic acid product from the mixture.

* * * * *